United States Patent
Mound

(10) Patent No.: US 7,924,414 B2
(45) Date of Patent: Apr. 12, 2011

(54) NON-HAZARDOUS BULK MATERIAL ANALYZER SYSTEM

(75) Inventor: Michael Mound, Baden (CH)

(73) Assignee: ABB Schweiz AG (CH)

( * ) Notice: Subject to any disclaimer, the term of this patent is extended or adjusted under 35 U.S.C. 154(b) by 659 days.

(21) Appl. No.: 11/684,972

(22) Filed: Mar. 12, 2007

(65) Prior Publication Data

US 2007/0263212 A1    Nov. 15, 2007

Related U.S. Application Data

(63) Continuation-in-part of application No. 11/474,477, filed on Jun. 26, 2006, now Pat. No. 7,310,581.

(60) Provisional application No. 60/836,379, filed on Aug. 9, 2006.

(30) Foreign Application Priority Data

May 10, 2006   (EP) .................................... 06405196

(51) Int. Cl.
  *G01J 3/44*   (2006.01)
  *G01N 21/00*   (2006.01)
(52) U.S. Cl. ........................... 356/73; 356/301; 356/326
(58) Field of Classification Search .................... 356/73, 356/301, 326, 440, 432
See application file for complete search history.

(56) References Cited

U.S. PATENT DOCUMENTS

| | | | |
|---|---|---|---|
| 4,026,717 A | 5/1977 | Harris et al. ................... 106/100 |
| 4,508,573 A | 4/1985 | Harris ............................ 106/100 |
| 4,749,273 A | 6/1988 | Reinhold | |
| 4,799,880 A | 1/1989 | McCoy ........................... 432/13 |
| 4,976,540 A | 12/1990 | Kitamura et al. ............... 356/38 |
| 5,410,154 A | 4/1995 | Broicher et al. | |
| 5,754,423 A | 5/1998 | Teutenberg et al. .......... 364/148 |
| 6,160,618 A | 12/2000 | Garner .......................... 356/318 |
| 6,491,751 B1 | 12/2002 | Watson .......................... 106/756 |
| 6,512,577 B1* | 1/2003 | Ozanich ........................ 356/73 |
| 6,690,464 B1* | 2/2004 | Lewis et al. .................. 356/326 |
| 6,709,510 B1 | 3/2004 | Young et al. .................. 106/745 |
| 6,771,369 B2 | 8/2004 | Rzasa et al. ................... 356/326 |
| 7,113,265 B1* | 9/2006 | Sarrazin et al. ................ 356/73 |
| 7,277,168 B2* | 10/2007 | Walker ........................... 356/317 |
| 7,508,501 B2* | 3/2009 | Zubkov et al. ................. 356/73 |
| 2003/0123056 A1 | 7/2003 | Barnes et al. ................. 356/300 |
| 2003/0197126 A1 | 10/2003 | Sato et al. | |
| 2004/0021861 A1* | 2/2004 | Lewis et al. .................. 356/326 |

(Continued)

FOREIGN PATENT DOCUMENTS

DE    4240094 A1    6/1994

(Continued)

OTHER PUBLICATIONS

European Search Report; Oct. 6, 2006; 7 Pages.

(Continued)

*Primary Examiner* — L. G Lauchman
(74) *Attorney, Agent, or Firm* — St. Onge Steward Johnston & Reens LLC

(57) ABSTRACT

A system for processing bulk materials, comprising at least one transport apparatus that conveys a stream of bulk materials from a first process position to a second process position, an illumination source that projects light on to a surface of the stream, and at least one spectrometer that captures light reflected, emitted, or absorbed by the stream.

37 Claims, 3 Drawing Sheets

U.S. PATENT DOCUMENTS

| | | | |
|---|---|---|---|
| 2004/0031335 A1 | 2/2004 | Fromme et al. | 73/865 |
| 2004/0207842 A1 | 10/2004 | Rzasa et al. | 356/328 |
| 2004/0232339 A1 | 11/2004 | Lanoue | 250/339.05 |
| 2005/0077471 A1 | 4/2005 | Edwards et al. | 250/360.1 |

FOREIGN PATENT DOCUMENTS

| | | |
|---|---|---|
| EP | 0463960 A1 | 1/1992 |
| EP | 0635138 B1 | 12/1997 |
| GB | 2111193 A | 6/1983 |
| WO | 0025115 A1 | 5/2000 |
| WO | WO 02/065072 | 8/2002 |
| WO | WO 02/065100 | 8/2002 |
| WO | WO 02/065101 | 8/2002 |
| WO | WO 02/065102 | 8/2002 |
| WO | WO 02/088811 | 11/2002 |
| WO | WO 2004/106874 | 12/2004 |
| WO | WO 2006/054154 | 5/2006 |

OTHER PUBLICATIONS

Advanced Spaceborne Thermal Emission and Reflection Radiometer; ASTER (Japanese Ministry of Economy, Trade and Industry and NASA); www.asterweb.jpl.nasa.gov; 83 pages.

Analytical Spectral Devices, Inc.; Field Spectrometry: Techniques and Instrumentation; Boulder, Colorado; 2001; 9 pages.

Analytical Spectral Devices, Inc.; Identification of raw materials by NIR reflectance; Boulder, Colorado; www.asdi.com; 8 pages.

Analytical Spectral Devices, Inc.; Introduction to NIR Technology; Boulder, CO; www.asdi.com; 10 pages.

Analytical Spectral Devices, Inc.; NIR Analysis of White Powder Samples; Boulder, Colorado; www.asdi.com; 4 pages.

Analytical Spectral Devices, Inc; Quantitative Analysis of Concrete Samples Via NIR; Bolder, Colorado; www.asdi.com; 2004; 7 pages.

Clark, R. N.; Spectroscopy of Rocks and Minerals, and Principles of Spectroscopy, in *Manual of Remote Sensing*, Chapter 1: vol. 3, *Remote Sensing for the Earth Sciences*, (A.N. Rencz, ed.) John Wiley and Sons, New York, p. 3-58, 1999; 67 pages.

CTR Carinthian Tech Research AG; Spectral Imaging Brochure; www.ctr.at; 2 pages.

Leetham, Darrell, et al.; Flexibility in Online Analysis; USA; www.thermo.com; 6 pages.

Perkinson, Maire-Claire et al.; Low Cost Hyperspectral Imaging From Space; England; 4 pages.

Stevens, Dave et al.; Recent Developments in Hyperspectral Imaging and their Significance as a New and Important Direct Exploration Tool; 26 pages.

Analytical Spectral Devices, Inc.; NIR Analysis of Concrete Samples; Boulder, Colorado; www.asdi.com; Date Uncertain; 12 pages.

Analytical Spectral Devices,Inc.; QualitySpec Pro; Boulder, Colorado; www.asdi.com; Date Uncertain, 4 pages.

Headwall Photonics Raman Explorer—Multi-Channel, Multi-Spectrum Imaging Spectrometer; www.HeadwallPhotonics.com; 2004; Headwall Photonics, Inc.; 4 pages.

Laser Induced Breakdown Spectroscopy—Wikipedia, The Free Encyclopedia; retrieved Apr. 12, 2006; 4 pages.

QCX/BlendExpert—Pile; "On-line PGNAA Analysis Combined with Advanced Software for Accounting, Data Presentation and Optimising"; FLSMIDTH AUTOMATION; Rev. Nov. 2002/2003; 2 pages.

* cited by examiner

NON-HAZARDOUS BULK MATERIAL ANALYZER SYSTEM

CROSS-REFERENCE TO RELATED APPLICATIONS

This application is a continuation-in-part of U.S. patent application Ser. No. 11/474,477 filed Jun. 26, 2006, now U.S. Pat. No. 7,310,581 claims priority of European patent application No. 06405196.4 filed May 10, 2006. The present application also claims the benefit under 35 U.S.C. §119 (e) of the U.S. Provisional Patent Application Ser. No. 60/836,379 filed on Aug. 9, 2006. All prior applications are herein incorporated by reference in their entirety.

FIELD OF THE INVENTION

This invention generally relates to spectral imaging, more particularly to spectral imaging of bulk materials in a dynamic process.

BACKGROUND OF THE INVENTION

Bulk materials are utilized and produced in industrial applications such as cement production, scrap material processing, and process waste handling. Bulk materials can be characterized as materials used in industrial applications that are transported in high volumes on a continuously moving means such as a conveyor belt after the materials are crushed or otherwise reduced in size for purposes of easier handling in downstream production. Bulk materials can further be characterized as raw materials that are combined in proportion and processed to form another material (such as pre-blended materials), the resulting combination of mixed raw materials (such as post-blended materials) in a homogeneous or non-homogeneous form, scrap materials, and process waste. Bulk materials can also be characterized as materials with low unit value (i.e., individual amounts less than one ton in weight have essentially very small commercial values). In order to achieve economical processing, large volumes are transported to the downstream production units where the relatively valuable mineral contents are separated, or the comminution processes reduce the mass to manageable particle sizes for chemical, hydrometallurgical, or pyroprocessing stages. Therefore, no one particle has more or less value than its neighbor (unlike high value particles that undergo separation as with contained precious metals or gemstones from mass materials), and all material is treated "in bulk." Typical bulk materials include heterogeneous masses of coarsely crushed mined or quarried bulk materials such as ores of limestone, bauxite, copper, zinc, lead, iron, silica, phosphate rock, potash, clay, rare earths. Other bulk materials transported similarly include scrap materials, chalk, coal and coke, alumina, marl, pyrite, fly ash, process waste, etc. Such bulk materials are utilized in process streams in which the bulk materials are fed or supplied from a source continuously, in batches, or over an extended period of time.

In some processes that utilize bulk materials, components or raw materials are transported from dispensing sources (such as bins or silos), mixed together, and processed to form a new material. Typically, bulk materials are transported through these processes in large volumes utilizing conveyor belts. A conveyor belt consists of two end pulleys, with a continuous flexible heavy-duty rubber, rubberized fabric, or metal composite belt that rotates about them in a continuous unending loop. The pulleys are powered, moving the belt and the loaded bulk material on the belt typically to another belt transfer point, or other belt system used in the specific manufacturing process forward at fixed or variable speeds. Many processes that transport high volumes of bulk materials use pneumatic tubes or air slides to transfer the bulk materials between process points.

During the transportation and processing of bulk materials, it becomes necessary to analyze the exact or average chemical or mineral content and composition of the bulk material for control purposes. Such analysis is especially necessary when the bulk materials are mixed, ground, or processed to form new materials. In the context of process waste, the characterization of bulk materials can be effective in diagnosing the effectiveness of a process and monitoring for contaminants. Acquiring sufficiently accurate and detailed knowledge of the physical and chemical state of a moving stream of bulk materials can be difficult and challenging.

As noted above, cement processing is characterized by the processing and formation of bulk materials. Cement can be formed by mixing and intergrinding different raw material components in the dry condition (dry process) or it may be done in water (wet process). A flow diagram for a cement manufacturing process is depicted in FIG. 1. In this typical version of the cement manufacturing process, one or more feeders 100-102 introduce crushed raw components on to conveyor belts 105-107. The type of raw components combined to ultimately form cement depends on the type of cement being produced and the composition of the raw components being utilized. Typical raw components include calcareous materials (such as limestone, marl, chalk, oyster shells, aragonite and the like), argillaceous materials (such as clay, shale, slate, slag, fly ash, sand, sandstone and the like), ferruginous material (such as mill scale, iron ore or pyrites), alumina (such as bauxite or materials high in alumina) and certain additives that contribute to the characteristics of the cement. In some parts of the world, the limestones, marls and the like that include the calcareous component may also include sufficient proportions of the argillaceous material, such as aluminum oxide and iron oxide, so that only siliceous materials need to be added. Siliceous materials can similarly contain argillaceous material so that such siliceous material may incorporate the needed aluminum oxides. Each raw component can have a different mass particle size. For instance, one raw component may have a greater relative particle size while another raw component may have a much smaller average particle size. As a result, the overall admixture of these components can differ in terms of different chemistry as well as widely different particle sizes.

The crushed raw components are typically conveyed to a second conveyor belt 115 and admixed on the conveyor belt 115 in predetermined proportions. The proportions in which the raw components are admixed can be controlled by the rate in which the feeders dispense the raw components and the rate at which the first conveyor belts transport the raw components. As a result, each of the raw components are admixed at different rates of quantity per unit time. Table 1 shows the relative mineral composition of a typical admixture:

TABLE 1

| Dry Basis Oxide | Composition Range* (%) |
|---|---|
| $SiO_2$ | 20 (5-25) |
| $Al_2O_3$ | 8 (0-8) |
| $Fe_2O_3$ | 8 (0-8) |
| CaO | 30 (25-55) |
| MgO | 6 (0-6) |
| $K_2O$ | 3 (0-3) |

TABLE 1-continued

| Dry Basis Oxide | Composition Range* (%) |
|---|---|
| Na2O | 3 (0-3) |
| SO3 | 3 (0-3) |

In dry processing, the admixed raw components are transported through a series of coarse and/or fine grinding mills 125. The mills integrate the raw components into a homogeneous mixture and dispense a coarse granulation, such as between 50 and 100 mesh, or a fine granulation, such as smaller than 100 mesh, respectively. The mills can be any kind of grinding apparatus, such as an industrial roller, rotary mill, ball mill, disc mill, cage mill, muller mill, high speed mill or the like. These mills dispense the resulting raw mixture onto subsequent conveyor belts 130, which transport the raw mixture to other mills or process stations. Upon completion of the processing of the raw mixture, the raw mixture is conveyed to a kiln 140.

During the transport of the raw components and the raw mixture from the feeders to the kiln other processing steps and apparatuses optionally may be included. These additional steps and apparatuses may be additional crushers, feeders that provide additional additives to the raw mixture, transport belts, storage facilities and the like.

The kiln can be vertically angled and mounted such that it can be rotated about its central longitudinal axis. The raw mixture is introduced at the top (or feed end) of the kiln and transported down the length of the kiln under the force of gravity. The kiln operates at temperatures on the order of 1,000 degrees Celsius. As the raw mixture passes through the kiln, the raw mixture is calcined (reduced, in chemical terms). Water and carbon dioxide are driven off, chemical reactions take place between the components of the raw mixture, and the components of the raw mixture fuse to form what is known as clinker. In the course of these reactions new compounds are formed. The fusion temperature depends on the chemical composition of the feed materials and the type and amount of fluxes that are present in the mixture. The principal fluxes are alumina ($Al_2O_3$) and iron oxide ($Fe_2O_3$), which enable the chemical reactions to occur at relatively lower temperatures.

The clinker thus formed is discharged typically onto a grate-type cooler. The cooled clinker is then transported by conveyor belt 145, where a feeder 155 dispenses and admixes gypsum to the clinker. The mixture is transported to a mill 165, which crushes the clinker and homogeneously mixes the gypsum into the composition forming a fine powder cement composition. The mill 165 dispenses the cement composition onto a conveyor belt 170 that transports the cement to silos 190, 195 for storage.

Wet systems involve processing the raw components through suitable crushers, grinders and mills either individually or as an admixed composition to the desired level of fineness. The raw components are then fed into water to form slurry. The slurry is transported to a storage tank for that purpose and is constantly agitated. At this stage the slurry can be tested and additives can be included. The slurry is then reduced to a desired fineness by feeding the slurry through suitable crushers, grinders and mills. The slurry is eventually fed into the kiln and processed as in the dry process procedure.

One important consideration in the creation of cement is that the proportion of components must be maintained within narrow limits. Differences in the amount of components introduced in the raw mixture and differences in the composition of the components formed during processing affects the quality and grade of cement. Other factors that influence the type of cement produced include temperature, residence time, size of the particles and intimacy of contact between the particles. As a result, care must be taken in making decisions to consider both upstream conditions and predict downstream results when any adjustments are made to the mix of raw components materials in order to achieve the desired result.

Traditionally, analysis and monitoring of either raw material components, blended materials such as the raw mixture, and processed cement has been accomplished by extracting samples from the continuous flow and transporting them either manually or via an automatic "tube post" pneumatic capsule sampling and conveying system from the sampling point to a central laboratory for analysis. The laboratory would then prepare and analyze the samples utilizing a variety of standard equipment and instruments. The results of these analyses are then used to adjust factors such as the rate at which the raw components are proportioned to achieve a desired blend recipe.

This arrangement, while providing high accuracies, is deficient because the aggregate time required for sampling, splitting, transport, preparation, and analysis can vary from a minimum of 15-30 minutes to an hour or more. During this delay, the stream of components and mixtures continue to be processed such that tons of the fast-moving bulk materials represented by each sample analyzed have long passed points of control and adjustment. The path followed by these materials from the feeders, along the conveyor belts, through the grinders and kiln and into the silos is a continuous flow (or stream). Any adjustments subsequently made to the process will not be able to correct deficiencies in raw mixtures and processed cement that have moved beyond positions in which corrective action may be taken. These adjustments will only affect raw components, raw mixtures and processed cement that are generated subsequent to the adjustments.

Another difficulty with the above is that this method does not provide a solution to potential problems that require prompt dynamic corrective actions. For instance, the rate of admixing raw components depends not only on the type of materials being mixed but also on the composition of those components. If a feeder contains raw components that lack compositional uniformity, the sample analysis may not be representative of the current stream. Thus, any adjustments that are made after a sample analysis may not be appropriate for the current components and respective composition of those components.

For instance, U.S. Pat. No. 4,026,717 describes a method for monitoring the production of cement in which samples are taken from the material flow stream at various points along the process. After the samples are processed by a coarse mill, a pre-kiln sampler using a bucket extracts samples every 15 seconds and deposits the samples on a second conveyor belt. The belt transports the samples to a blending mill that collects develops a composite sample over 15 minute time period. A conveyor then transports the composite sample to an x-ray analyzer. These samplers are also disclosed for extracting samples from the kiln and the clinker cooling system.

Analysis of cement bulk materials can also require knowledge of the oxides or mineralogical phases (molecular polymorphs), or a standard calculated module based on the quantity of the oxides (or other desired measured properties) present, for standard quality control. Some analytical devices used may not measure either oxide or actual phases directly, but only the elemental values.

A few methods to achieve elemental, and thereby, oxide forms of the chemical constituents of the various raw or blended materials have been utilized. They are, however, limited in terms of practical application and mainly make use of atomic events based upon neutron activation via nuclear activation. These so-called Prompt Gamma Neutron Activation Analysis (PGNAA) systems require either radioactive isotopes for neutron flux, such as the isotope of Californium, $Cf_{252}$, or a neutron generator (tube). In these cases, the introduced neutrons cause momentary and temporary disequilibrium of the nuclei of contained materials resulting in emission of gamma radiation signatures as a reaction to restore equilibrium. Neutron activation systems apply a potentially hazardous (to humans) technique which requires protective permanent careful shielding to avoid and minimize direct or indirect exposure and frequent costly isotope or generator tube replacements. The short half-life of $Cf_{252}$ at only approximately two and a half years and the requirement for replacement of neutron tube generators, normally every one to one and a half years, represent both expensive maintenance costs as well as the need to address increasing difficulties in convincing authorities of the public safety in transport and operation of both these types of neutron sources. Further, the resultant gamma radiation from the neutron activation of bulk materials that is caused by neutron flux bombardment of the nuclei of the irradiated materials represents potential additional health and environmental hazards. Other on-line techniques that have been attempted, such as high-power X-ray tube systems, or X-ray diffraction systems, may also require strict adherence to local regulatory authorities. In some venues, the presence of certain of these various classes of all of such devices may be restricted or prohibited altogether.

What is needed is a system and method for analyzing bulk materials that provides real-time analyses for rapid and real-time control. It is critical that the apparatus and method analyzed the bulk materials as they pass through. It would be beneficial if such an apparatus and method analyzed the bulk materials in the process stream. Additionally, such apparatus and method must not alter or touch (either physically or chemically) the streaming bulk materials. As a result, the bulk materials analyzed are to pass uninterruptedly along the process flow. Another benefit would be for the apparatus and method to implement the analysis of the bulk materials as it is transported on a moving conveyor belt from one process station to the next.

SUMMARY OF THE INVENTION

It is therefore an objective of the present invention to provide a robust, consistent, real-time bulk material analyzing system for identifying and quantifying the elemental, chemical, and mineralogical characteristics of a varying bulk material passing unobstructed and undisturbed under or through a detector array.

It is another objective of the present invention to provide an analyzing system that does not interrupt or extract sample materials in any amounts from the process stream.

It is a further objective of the invention to provide a bulk material analyzing system using non-hazardous sources of excitation exclusively.

It is still a further objective of the invention to provide a method for processing bulk materials and controlling the processing of monitored bulk materials.

These and other objectives are achieved by a system for processing bulk materials with at least one transport apparatus that conveys a stream of bulk materials from a first process position to a second process position, an illumination source that projects light onto a surface of the stream, and at least one spectrometer that captures light reflected, emitted, or absorbed by the stream. Preferably the illumination source projects a light spot or illuminated area on to a fixed position beneath or through which the surface of the stream passes and the spectrometer captures spectral signatures of the bulk material. It is also preferable that the spectral signatures indicate the reflectance, emissions, and/or absorption of light by the bulk material.

It is a further aspect of the invention to provide a control unit that communicates with the spectrometer(s) and receives spectral signatures captured by the spectrometer(s). Preferably, the control unit analyzes the measurements taken by the spectrometer by querying a database comprising stored spectral signatures and comparing the measured spectral signatures to the stored spectral signatures.

It is another aspect of the invention for the control unit to communicate with a process apparatus or a transport apparatus, each comprising at least one operation setting, and transmits instructions to the process apparatus or transport apparatus to alter the operation setting. These operation settings can control the manner in which a first material is combined with a second material, the rate at which a first material or a second material is dispensed, the rate at which a first material or a second material is transported, or whether the process apparatus or the transport apparatus is activated.

It is still a further aspect of the invention for the system to comprise at least one bulk material dispenser that dispenses a stream of bulk materials, at least one transport apparatus that conveys the stream of bulk materials dispensed by the bulk material dispenser, and at least one process apparatus that modifies the stream of bulk materials from a first material to a second material. The (at least) one process apparatus can mix or grind the stream of bulk materials, dispense a third material to combine with the stream, thermally heat the stream, or execute further process actions.

It is yet another aspect of the invention for the at least one spectrometer to capture light reflected, emitted, or absorbed by the bulk material streaming prior to or after processing by a process apparatus.

These and other aspects of the invention and its particular features and advantages will become more apparent from consideration of the accompanying description.

DETAILED DESCRIPTION OF THE INVENTION

The present invention will now be described more fully hereinafter with reference to the accompanying drawings which illustrate preferred embodiments of the invention. This invention may, however, be embodied in many different forms and should not be construed as limited to those set forth herein. Rather, these embodiments are provided so that this disclosure will be thorough and complete, and will fully convey the scope of the invention to those skilled in the art. Like numbers refer to like elements throughout.

In a preferred embodiment of the present invention, a bulk material processing system incorporates a real-time bulk material analyzing system that utilizes a consistent level of brightness of white light, an array of splitting and collecting spectral components using, for example, collimating gratings, detectors, or generators, and an array of one or more detectors within one or more small, robust spectrometers to provide spectral signatures. The analyzing system captures spectra of both reflectance and absorptive translational and rotational vibrations from the bulk material mass illuminated by the white light.

Reflectance and emission spectroscopy of natural surfaces are sensitive to specific chemical bonds in materials, whether solid, liquid or gas. Spectroscopy has the advantage of being sensitive to both crystalline and amorphous materials, unlike some alternative optically limited diagnostic methods. Spectroscopy is also adaptable for providing analysis materials at variable ranges and in variable geometries.

Figure 2:
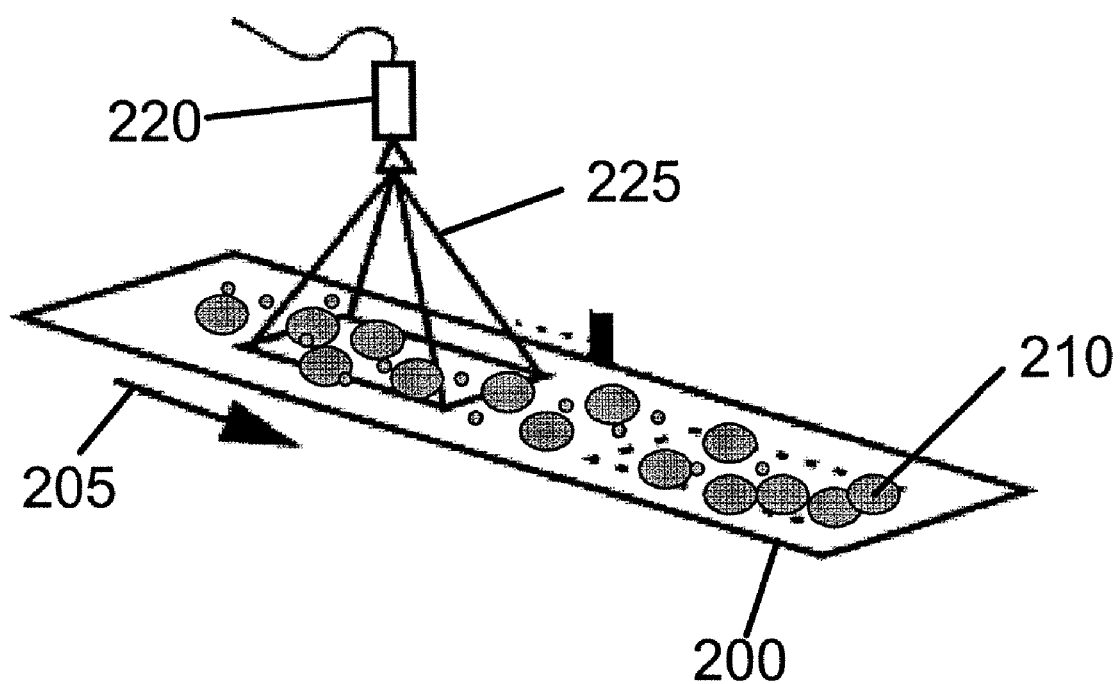
FIG. 2 is a depiction of bulk material analyzer positioned over a moving conveyor belt loaded with bulk materials.
Figure 3:
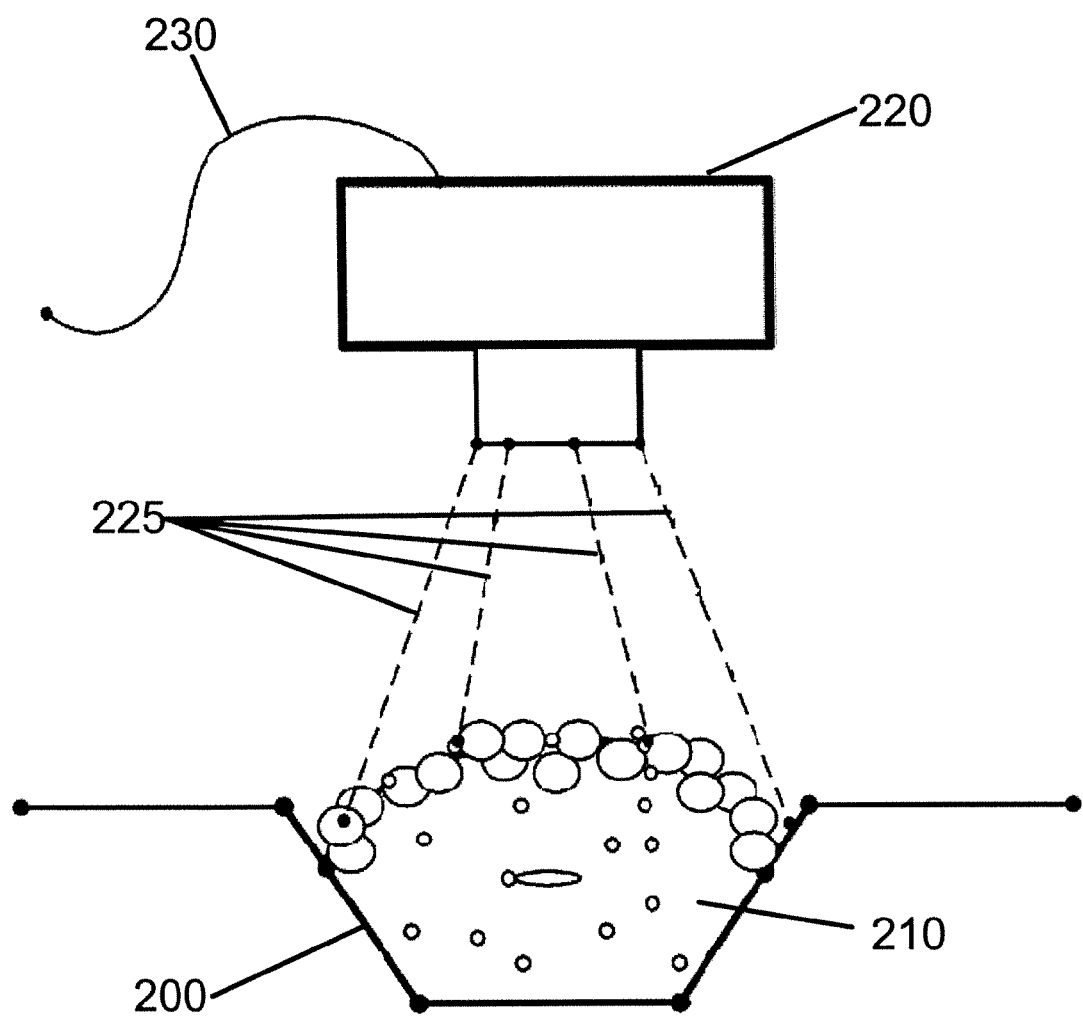
FIG. 3 is a depiction of a cross-sectional view of the profile of a conveyor belt loaded with bulk materials and an analyzer device positioned above the belt.

FIGS. 2-3 depict portions of systems for processing bulk materials. These systems utilize a bulk material analyzer placed over a transport apparatus such as a conveyor belt or pneumatic transfer that transfers the bulk material from one process point to another.

FIGS. 2 and 3 in particular depict bulk materials 210 loaded and transported by a conveyor belt 200. These bulk materials 210 are a non-uniform distribution of materials on conveyor belt 200 with variable particle sizes, bed height (i.e. the height of the bulk materials above the belt surface) and composition. FIG. 3 depicts a cross-sectional view of the profile of conveyor belt 200 loaded with bulk materials 210. This figure shows that the amount and weight of bulk materials 210 on belt 200 causes the belt to deflect towards the center of the belt 200. This typically results in a non-uniform bed height and distribution of bulk materials above belt 200.

FIGS. 2 and 3 also depict bulk material analyzer 220 positioned over conveyor belt 200 that projects white light 225 on to the surface of bulk material 210. The bulk material analyzer 220 measures the spectral signature of bulk materials 210 based on light that is reflected, emitted and absorbed by bulk materials 210, which is discussed in more detail below.

The bulk material analyzer comprises a spectrometer with an illumination source and a control unit. The bulk material is spread across the surface area of conveyor belt to form a bulk material bed load. The bulk material bed has an upper surface area facing the direction of the inventive bulk material analyzer and a lower surface area adjacent to the conveyor belt. The height of the bulk material on the conveyor belt can very depending on the material distribution, however the upper surface area can be attributed as having a nominal bed height. The bulk material can comprise a combination of individual components or a single component. Either can be of varying mass, particle size and composition. As the conveyor belt moves, bulk material streams beneath the bulk material analyzer such that the components of the bulk material beneath the bulk material analyzer changes. Illumination source emits white light and is positioned somewhere in the vicinity of the spectrometer. The illumination source projects a beam of light onto the bulk material forming an illumination spot that can be a variety of forms such as a wide circle, narrow band or a thin slit. The illuminated spot can also be formed on a portion of the upper surface area of the bulk material bed or across the entire width of conveyor belt 400. The illumination source may comprise one or more light emitters. The white light emitted by the illumination source may be set to different intensities and frequencies. This will act to further enhance reflectance, emittance and absorptive optical phenomena resulting in discrete spectral signatures as light is reflected, emitted or absorbed providing characteristic and identifiable wavelengths. Further, the illumination source can be placed at a defined distance from the nominal bed height such as 2 meters.

The spectral sensor may comprise a variety of optical components. A front lens may be installed at a predefined height above the conveyor belt 400. FIG. 2 further shows a scanned area which represents the area of reflected light from bulk material that is collected by the spectrometer(s) using an image sensor such as a CMOS or CCD device. The distribution of pixels along the y-axis of the image sensor corresponds to the wavelength of the reflected or emitted energy from the bulk material. The distribution of pixels along the x-axis of the image sensor can represent the location of measurement. Each component of the bulk material that is captured in the scanned area has its own spectral signature. The image sensor produces an output signal that is processed by a control unit connected to the spectrometer. The control unit preferably comprises a computer having at least one processor and memory with a plurality of databases. The control unit can further include a means for displaying information, like a monitor, and can have a communication link to process tools, which is described in more detail below. The output signals can be transmitted via a fiber optic or a high bandwidth cable or radio frequency link.

As bulk material passes by the spectrometer, scans can be taken continuously, in regular periods or on demand. Periodic scans are taken at regular time intervals enabling regular measurements of various areas of the scanned materials. Periodic or continuous scans can be used to collect data on the bulk material as it passes beneath the spectrometer.

To facilitate the spectral analysis the resolution of the two-dimensional output array can be reduced across the x-axis. In this embodiment one such particularly simple embodiment of the inventive bulk material analyzing system, the resolution of the output array across the x-axis is reduced so that only one spectral signature is forwarded to the control unit. This single spectral signature is then analyzed and compared to a set of previously recorded and stored spectral signatures of possible material composition. This embodiment is applicable where the distribution of bulk materials is homogeneous, such as the raw mixture in cement processing, and the distribution of different materials across the conveyor belt may not be as critical as the composition of the bulk material, i.e. the existence of specific ingredients in the right quantity, matters. This technique is preferably used in applications when a small number of possible ingredients are to be observed.

In one version of the inventive bulk material analyzing system, only white light is required for constant illumination to provide a source for infrared splitting to cause reflective and absorptive spectral structure of the contained bulk materials. Infrared, including NIR (near infra-red), VNIR (Visual near infrared), SWIR (Short-Wave Infrared), and TIR (Thermal Infra-red), span a wavelength range of 250 to 2500 nanometers (nm) for the purposes of compositional characterization of materials. When subjected to illumination by a bright, white light source, the choice of examining any range within the electromagnetic spectrum is dependent on the materials being examined. In the case of inorganic materials (rocks, ores, etc), the choice of where in the range of 250 to 2500 nanometers can be more important because the degree of translational and rotational vibration is highly variable depending on the molecules of interest. If calcium, iron, aluminum, silicon, sulphur, alkalis, free oxides, and so on, are of interest (in their combined molecular or crystallographic forms), different parts of the wavelengths of the infrared spectrum will have to be examined. In a preferred embodiment the light source emits light over the entire 250 to 2500 nanometer. Sub-ranges, such as 200-1000 nm, may not be effective for bulk material with a diverse set of components because the spectrum may not capture a spectral signature adequate to characterize the bulk material. Examining the spectra over the full range enables a diverse set of molecules and elements, a characteristic of many bulk materials, to be analyzed because the reflective and absorptive responses to illumination among the elements/molecules/mineral phases of interest produce spectra of different amplitudes along the wavelengths possible.

As bulk materials can be in oxidized, reduced, elemental, or crystalline/molecular states, it is useful to recognize these conditions and convert them to a desired result for reporting purposes. Oxides can be reported via built-in calculations of standard conversions from elements to their oxide forms. As an example: aluminum, Al, can be converted to report aluminum-oxide, $Al_2O_3$, by an automatic conversion factor of 1.8895 times the reported quantity of the element Al. Similar conversion factors are readily made for reporting purposes for any detected element of interest. These conversion factors are standard for reporting results based on known chemical properties of all elements in their atomic or molecular forms and can be provided as desired by users in any format to report results of analyses using simple calculations built into the device software.

In another embodiment bulk material analyzers or spectrometers are used to effectively provide for the strongest s/n (signal to noise ratio) for several spectral ranges within the wavelengths of the elements to be analyzed. In an arrangement of several spectrometers, each of the spectral sensors can be arranged so that an imaginary straight line extends from the center of each sensor to a common point on the bulk material to be analyzed. Alternatively, overlapping spectral reports can be made by precise spectrometer positioning, if necessary, in order to provide a scanned strip-swath across the width of the conveyor belt. As such, each spectrometer can identify and characterize spectral signatures for different portions of spectral range. For instance, one spectrometer can identify a spectral signature for the 250-1000 nm range, while another spectrometer can identify a spectral signature for the 1000-2500 nm range. This technique overcomes the limitations of spectral range restrictions of individual spectrometers. Thus, the requirement of the full span of the IR spectrum is met as different elemental/mineralogical components respond with stronger signals at different wave length regions.

Any number of chemometric techniques may be used to provide for fitting spectra thus obtained to the stored library of spectra. In the initial calibration of the device, spectra are stored of expected masses of particular bulk materials to cover all possible ranges of concentrations and mixtures (blends) of elemental contributors to the recovered and resolved spectra. Such acquired spectra are "compared" to the stored spectra to define how the acquired spectra compare to a predicted oxide or mineralogical phase array. The "goodness" of the fit of the acquired spectra and its height difference relative to the selected standard spectral library stored in the device determine both content and quantity of the elements/ oxides/phases based on spectral regions and peaks.

Both reflectance and absorptive responses provide characteristic and unique signals for each area of interest, but do not do so either uniformly or with the same strengths. Chemometrics provides a statistical solution to create a baseline from which to resolve the important spectral information to match (i.e., fit) to a modeled calibration library in a meaningful manner. A continuum of the combined signal of interest along with the additional responses of "noise" must be separated so as to detect the highest possible S/N (signal-to-noise) ratio. This ratio can vary from several tens to several thousands, depending on where in the dynamic range of wavelengths the spectrometer is configured.

The spectrometers and their contained possible combinations of gratings, beam splitters, detectors, and optical fiber connections, as well as light sources are preferably packaged in a scanning housing fixed at a predetermined height above the moving conveyor belt. The housing thus described is arranged so as to be located normal to the normal forward or backward directional movement of the belt and its material load.

Applications of this technique are suitable for, but not limited to materials transported by industrial conveyors such as: limestone, shale, bauxite, iron ore, copper ore, zinc ore, lead ore, metalliferous (ferrous and non-ferrous) ores, silica, phosphate rock, potash, clay, bentonite, pharmaceuticals, manganese, rare earths, scrap materials, chalk, coal and coke, alumina, marl, pyrite, fly ash, slurries of any of the above, fertilizers containing phosphates, ammoniacal components, potassium/potash, industrial minerals (ceramics, glass-making raw materials, refractories), magnesium compounds, cobalt, nickel, titanium, chrome, and tungsten.

In operation, the control unit compares the spectral signature of each scan to a set of stored calibrations representing expected concentrations of previously characterized standards. This is done in real time with the help of computer software. As a result, the materialistic characteristic of the bulk material distributed across the conveyor belt is identified.

In the next step, the control unit gathers the information of all scans to get the overall distribution of material within the scanned bulk material. Specific elements or their oxides can thereby be identified as to presence and characterized as to concentrations via intensities of detected and recognized spectral signatures.

The control unit can comprise one or more algorithms with diagnostic capabilities in which it is determined whether the spectral signature complies with stored spectral signatures in its database that correspond to each specific bulk material. With this feature the control unit can be programmed to determine whether the measured spectral signature for a particular measurement location, each individual measurement location, or a spectral signature that represents a combination of measurement locations, matches or falls within acceptable tolerances to one or more stored spectral signatures. The analysis can also include determining whether the minerals or elements in the bulk material are deficient or excessive in the amount or proportion. Based on any determination of deficiency or excess, the control unit can perform the appropriate algorithm to predict the characterization of a material to be formed using the bulk material, such as an end or mid process composition.

The diagnostic capabilities can further include the ability to determine what form of corrective action can or should be made to a process. The control unit can query a database of corrective actions that may be taken to address the problem. The corrective actions can include adjusting the feed rate of the bulk material, activating or adjusting a second source that will provide additives to compensate for the deficiency, or adjusting the parameters of subsequent process apparatuses, such as a kiln. Upon determining one or more appropriate corrective actions, the control unit may display the corrective action on a common means such as a display.

Alternatively, the control unit can be coupled to one or more processing apparatuses and comprise the ability to issue instructions to the apparatuses. For instance, the control unit could instruct a raw component feeder or transfer belt to slow or increase the rate at which the raw component is mixed with other components. The control unit could instruct a second component source, such as an additive source, to introduce additional minerals or molecules to correct the measured discrepancy. The second source can be disposed at a point in the process before the bulk material is analyzed or after the bulk material is analyzed. If this second source dispenses an additive before the bulk material is analyzed, this will enable the analyzing system to quickly determine if the corrective action is effective in resolving the deficiency. If the second source dispenses an additive after the bulk material is analyzed, this will enable the bulk material identified as being deficient to be corrected avoiding the production of deficient material.

The bulk material analyzing system can also be integrated at process positions after bulk materials are admixed together, after bulk materials ground or mixed into a homogeneous mixture, after bulk materials are processed to form a new composition, and at process points in which process waste is dispensed from the manufacturing process. As described above, the analyzer can be integrated over a transport apparatus such as a conveyor belt and analyze the material either periodically or continuously as the material streams past the analyzer. The analyzer gathers the spectral signatures of the streaming material and determines whether the measured signature complies with the stored signatures. In event that analyzer determines that there is non-compliance, the analyzer can determine the appropriate corrective action and display such corrective action for an operator or transmit instructions to an appropriate machine utilized in the process to adjust the machine's operating parameters.

The analyzer can also be integrated at a post process position for purposes of identifying processed materials of different grades or quality. In such an embodiment the analyzer is positioned over a conveyor belt that transports the materials formed by the process. The analyzer gathers the spectral signatures of the streaming material and determines whether the measured signature corresponds with stored signatures of different grades or quality. In event that analyzer identifies the material as having a particular grade or quality, the analyzer can display such grade or quality for an operator or transmit instructions to a switch or other binning apparatus that will divert or direct the identified material to an appropriate storage facility.

Figure 1:
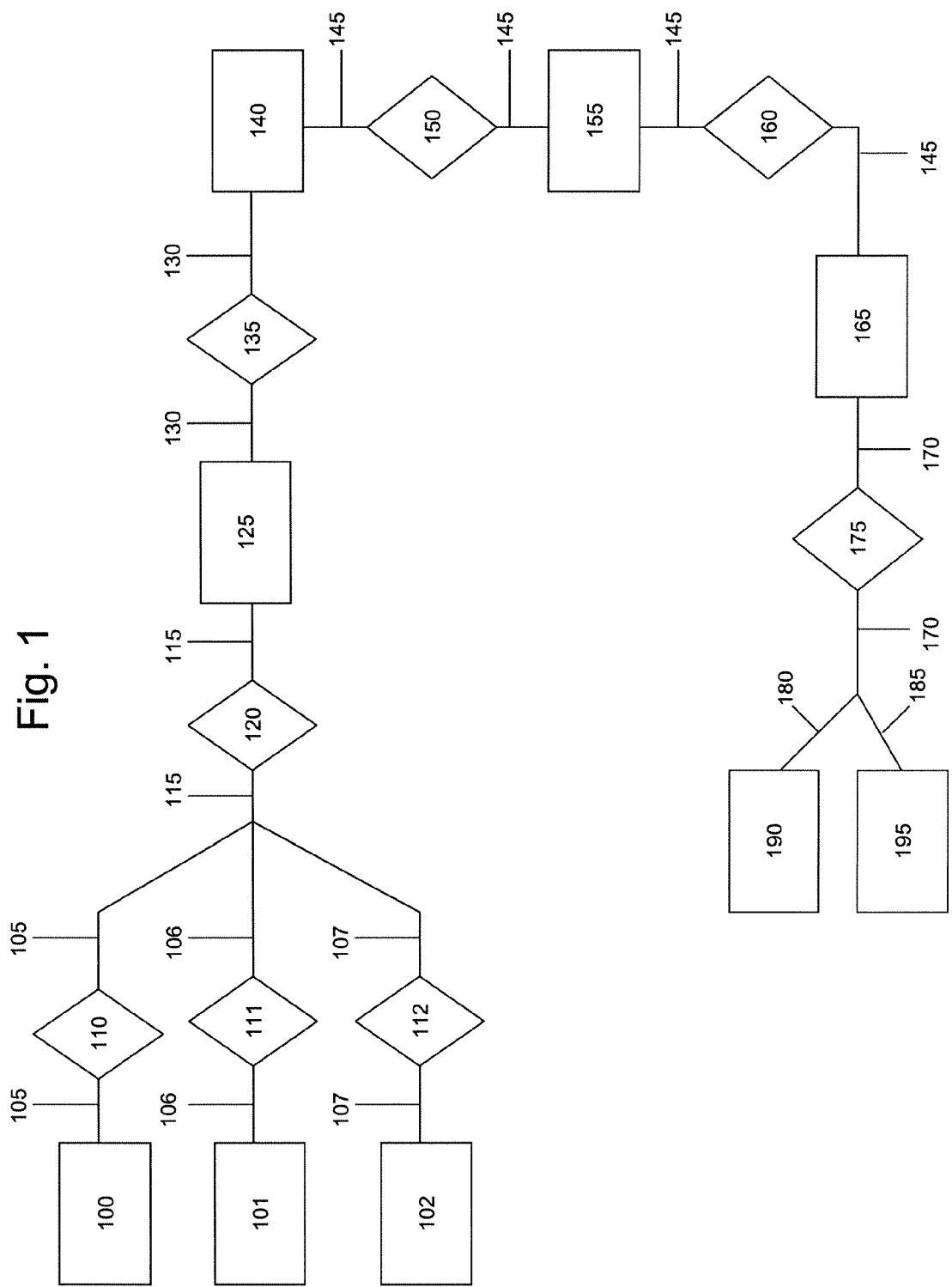
FIG. 1 is flow chart depicting the process steps of a common method for manufacturing cement.

In an exemplary embodiment the inventive bulk material analyzing system is integrated into a process for manufacturing cement as shown in FIG. 1. Analyzing systems monitor the streaming flow of raw components dispensed from feeders and transported by conveyor belts for admixture (110-112), the admixture transported to a grinder or mill (120), the raw mixture transported to a kiln (135), the clinker dispensed from the kiln (150), the mixture of clinker and gypsum transported to a mill (160), and the cement composition transported to silos for storage (175). As the bulk materials are transported along a conveyor belt between each process point the analyzing systems monitor the streaming flow. In the event that an analyzing system determines that the spectral signature of a bulk material is non-compliant, the analyzing system can alert an operator of such a condition or instruct a process apparatus, such as a raw component feeder 100-102, a conveyer belt controller, a grinder 125, 165, an additive feeder 155, or a kiln 140, to alter its process parameters. In order to assure that resulting composition of the cement is maintained according to specifications, the analyzing systems can utilize a control algorithm that obtains real-time chemistry of the bulk materials independently and collectively from results reported by the analyzing system and provide information or issue instructions that correct for more or less richer or poorer grades of components (according to the contained mineral chemistry) by additions of each material as demanded.

Table 2 shows the accuracies normally expected for dynamic performance of this cement manufacturing process which are:

TABLE 2

| Dry Basis Oxide | Accuracy (RMSD, 1 hour) (%) |
|---|---|
| SiO2 | 0.33 |
| Al2O3 | 0.30 |
| Fe2O3 | 0.08 |
| CaO | 0.32 |
| MgO | 0.29 |
| K2O | 0.21 |
| Na2O | 0.11 |
| SO3 | 0.20 |

Table 3 shows the conversion factors from oxide to element from an elemental analysis, for reporting purposes:

TABLE 3

| Dry Basis Oxide | Conversion factor (elemental) |
|---|---|
| SiO2 | 2.1393 |
| Al2O3 | 1.8895 |
| Fe2O3 | 1.4297 |
| CaO | 2.4973 |
| MgO | 1.6581 |
| K2O | 1.2046 |
| Na2O | 1.3480 |

During the transportation of dry bulk materials over a conveyor belt in a cement process, moisture content in the bulk materials can exceed 5-8% (liter weight %) as the bulk materials are exposed to ambient moisture. During processing, the moisture content is normalized by using a moisture meter (usually a phase-shift microwave device) that communicates with the analyzing system. The control unit receives the moisture data from the meter and applies a correction factor to the spectral signature in order to improve the accuracy of the spectral signature. If moisture can be guaranteed to not exceed 4-5%, then a moisture meter may not be necessary and a standard correction factor can be utilized.

In order to integrate the bulk material analyzing system into a process environment, the analyzing system needs to be calibrated for the type of bulk materials to be analyzed. In the cement manufacturing process, the calibration range needs to be broadened to cover low—as well as high—grade limestone, because the presence of MgCO3 in impure limestones is important to quantify when blending with higher grades, as too much MgO (exceeding 2.5%, for example) is a genuine quality problem. Such a cement manufacturing process typically requires five calibration standards of the type of bulk materials to be analyzed at each process point.

Instead of cement process samples, dilutions may be used to prepare a calibration. This can be accomplished by using a neutral diluent matrix, such as pure limestone of known concentrations of CaO, for example, to make the factoring simple.

A range of calibration samples should encompass the typical ranges shows to avoid compromising the analyzer's ability to fit variations into the resultant calibration curve when alternative and (normally) widely varying materials are incorporated into the mix, as one would expect in a typical plant environment. With increasing use of alternative raw materials, the need for analysis increases. If one could expect a narrow bandwidth in concentrations of these key oxides, the need for monitoring would be slight, whereas an analyzer calibrated to capture variations in a broad range (within reasonable limits, of course) becomes more beneficial.

Since the materials will vary in densities, either volumetric or gravimetric measures should be determined. If the samples thus prepared for this purpose are insulated from degradation or deterioration (enclosed in sealed plastic, or similar), they should remain more or less immutable. This type of information as to sample results (offline) is typically provided beforehand by the plant's on-site central laboratory, and the results are incorporated into the plant control system (may also be manually implemented).

The above processes for bulk materials and the bulk material analyzing system are beneficial because they provide a real-time system and method for monitoring and controlling bulk material processes. The bulk material analyzing system is low cost, low maintenance, simple to use and control, versatile, non-hazardous, and robust. The low cost is attributed to the fact that an end-user price is expected to be a fraction of that of conventional neutron, i.e., PGNAA, on-line analyzers, and the accompanying simplicity of its use and maintenance of the system. These aspects and benefits are due to the fact that only the illuminator lamp needs changing periodically, thereby eliminating the need for retaining on-site technical expertise. The analyzing system also offers a versatile system that can identify a large number of different elements and mineral phases (polymorphs) which can be measured simultaneously both qualitatively and quantitatively. The analyzing system also has the ability to be non-hazardous in nature as no X-ray or neutron activation systems sources are used to excite the material to be analyzed.

Although the invention has been described with reference to a particular arrangement of parts, steps, features and the like, these are not intended to exhaust all possible arrangements, parts, steps or features, and indeed many other modifications and variations will be ascertainable to those of skill in the art.

What is claimed is:

1. A system for processing bulk materials, comprising:
   at least one transport apparatus that conveys a stream of bulk materials from a first process position to a second process position;
   an illumination source that projects light on to a surface of the stream;
   at least one spectrometer that captures a spectral signature of the bulk materials reflected by the stream;
   a control unit connected to the spectrometer which processes the spectral signature and analyzes the spectral signature captured by the spectrometer;
   wherein the control unit communicates with a process apparatus or a transport apparatus, each comprising at least one operation setting, and transmits instructions to the process apparatus or transport apparatus to alter the operation setting based on the analysis of the spectral signature.

2. The system of claim 1, wherein the illumination source projects white light.

3. The system of claim 1, wherein the illumination source projects light onto a fixed position through which the surface of the stream passes.

4. The system of claim 1, wherein the spectral signatures indicate the emission, reflectance, and absorption of light by the bulk material.

5. The system of claim 1, wherein the control unit queries a database comprising stored spectral signatures and compares the measured spectral signatures to with stored spectral signatures.

6. The system of claim 5, wherein the control unit determines whether the measured spectral signatures are within acceptable manufacturing tolerances.

7. The system of claim 1, wherein the operation setting controls the manner in which a first material is combined with a second material.

8. The system of claim 1, wherein the operation setting controls the rate at which a first material or a second material is dispensed.

9. The system of claim 1, wherein the operation setting controls the rate at which a first material or a second material is transported.

10. The system of claim 1, wherein the operation setting controls whether the process apparatus or the transport apparatus is activated.

11. A system for processing bulk materials, comprising:
    at least one transport apparatus that conveys a stream of bulk materials from a first process position to a second process position;
    an illumination source that projects light on to a surface of the stream;
    at least one spectrometer that captures a spectral signature of the bulk materials reflected by the stream;
    a control unit connected to the spectrometer which processes the spectral signature;
    at least one bulk material dispenser that dispenses a stream of bulk materials;
    at least one transport apparatus that conveys the stream of bulk materials dispensed by the bulk material dispenser; and
    at least one process apparatus that modifies the stream of bulk materials from a first material to a second material.

12. The system of claim 11, wherein the at least one process apparatus mixes or grinds the stream of bulk materials.

13. The system of claim 11, wherein the at least one process apparatus dispenses a third material that is combined with the stream of bulk materials.

14. The system of claim 11, wherein the at least one process apparatus thermally heats the stream of bulk materials.

15. The system of claim 11, wherein the at least one transport apparatus conveys the first material to the at least one process apparatus.

16. The system of claim 15, wherein the at least one spectrometer captures a spectral signature reflected by the first material on the at least one transport apparatus.

17. The system of claim 11, wherein a second transport apparatus conveys the second material dispensed by the at least one process apparatus.

18. The system of claim 17, wherein the at least one spectrometer captures a spectral signature reflected by the second material on the at least one transport apparatus.

19. The system of claim 1, wherein the at least one spectrometer comprises a first spectrometer and a second spectrometer that each capture a spectral signature reflected by the stream.

20. The system of claim 19, wherein the spectral signature captured by the first spectrometer corresponds to first frequency range and the tight spectral signature captured by the second spectrometer corresponds to a second frequency range.

21. The system of claim 1, wherein the at least one apparatus is a conveyor belt.

22. The system of claim 1, wherein the second process position modifies the bulk material from a first material to a second material.

23. The system of claim 1, wherein the first process position dispenses the bulk material on to the conveyor belt.

24. A method for processing bulk materials, comprising:
streaming at least one bulk material from a first process position to a second process position;
projecting light on to a surface of the stream;
capturing a spectral signature of the bulk material reflected by the stream;
processing the spectral signature and analyzing the spectral signature;
instructing a process apparatus or a transport apparatus to alter an operation setting based on analyzing the spectral signature.

25. The method of claim 24, wherein the step of capturing the spectral signature reflected by the stream is periodic.

26. The method of claim 24, wherein the step of capturing the spectral signature reflected by the stream is continuous.

27. The method of claim 24, further comprising the step of dispensing the at least one bulk material transported by a transport apparatus prior to the step of streaming at least one bulk material.

28. The method of claim 27, wherein the at least one bulk material is a conveyor belt.

29. The method of claim 27, wherein the at least one bulk material placed on the transport apparatus is non-uniformly distributed on the transport apparatus.

30. The method of claim 27, wherein the at least one bulk material placed on the transport apparatus forms a variable bed height.

31. The method of claim 24, wherein the bulk material comprises a non-uniform particle size.

32. The method of claim 24, further comprising the step of altering the manner in which a first material is combined with a second material.

33. The method of claim 24, further comprising the step of altering the rate at which a first material or a second material is dispensed.

34. The method of claim 24, further comprising the step of altering the rate at which a first material or a second material is transported.

35. The method of claim 24, further comprising the step of activating or deactivating the process apparatus or the transport apparatus.

36. The method of claim 24, wherein the second process position modifies the stream of at least one bulk material from a first material to a second material.

37. The method of claim 24, wherein the first process position modifies the stream of at least one bulk material from a first material to a second material.

* * * * *